US007871621B2

(12) United States Patent
Takeda et al.

(10) Patent No.: US 7,871,621 B2
(45) Date of Patent: Jan. 18, 2011

(54) ANTI-HBS MONOCLONAL ANTIBODY

(75) Inventors: Kazuhiko Takeda, Fujiidera (JP); Tadahiro Kajita, Abiko (JP); Ayumi Asaeda, Akashi (JP)

(73) Assignee: Sysmex Corporation, Hyogo (JP)

( * ) Notice: Subject to any disclaimer, the term of this patent is extended or adjusted under 35 U.S.C. 154(b) by 347 days.

(21) Appl. No.: 11/435,835

(22) Filed: May 18, 2006

(65) Prior Publication Data

US 2006/0264604 A1    Nov. 23, 2006

(30) Foreign Application Priority Data

May 18, 2005  (JP)  ............................ 2005-146091

(51) Int. Cl.
*A61K 39/42* (2006.01)
*C07K 16/00* (2006.01)
(52) U.S. Cl. .............. 424/149.1; 424/142.1; 424/133.1; 530/388.15; 530/388.3; 530/388.1
(58) Field of Classification Search ........................ None
See application file for complete search history.

(56) References Cited

U.S. PATENT DOCUMENTS

| 5,856,084 A | 1/1999 | Karayiannis et al. |
| 6,030,616 A | 2/2000 | Waters et al. |
| 2004/0219154 A1 | 11/2004 | Jolivet-Reynaud et al. |

FOREIGN PATENT DOCUMENTS

| WO | WO 97/40164 | * 10/1997 |
| WO | WO 97/40164 A1 | 10/1997 |

OTHER PUBLICATIONS

Karthiggesu V. et al. "A hepatitis B virus variant found in the sera of immunised children induces a conformational change in the HBsAg "a" determinant". J Med Virol. Aug. 1999;58(4):346-52.*

Paulij WP et al "Localization of a unique hepatitis B virus epitope sheds new light on the structure of hepatitis B virus surface antigen". J Gen Virol. Aug. 1999;80 ( Pt 8):2121-6.*

Jolivet-Reynaud et al, "Localization of Hepatitis B Surface Antigen Epitopes Present on Variants and Specifically Recognised by Anti-Hepatitis B Surface Antigen Monoclonal Antibodies", Journal of Medical Virology, vol. 65, No. 2, Oct. 2001, pp. 241-249, XP002195005.

Cooreman et al, "Characterization of the Reactivity Pattern of Murine Monoclonal Antibodies Against Wild-Type Hepatitis B Surface Antigen to G145R and Other Naturally Occuring "a" Loop Escape Mutations", Heptatology, vol. 30, No. 6, Nov. 1999, pp. 1287-1292, XP001015475.

Mengji Lu, et al, "De Novo Infection in a Renal Transplant Recipient Caused by Novel Mutants of Hepatitis B Virus Despite the Presence of Protective Anti-Hepatitis B Surface Antibody", Journal of Infectous Diseases, vol. 187, Apr. 15, 2003, pp. 1323-1326.

Klaus M. Weinberger, et al, "High Genetic Variability of the Group-Specific α-Determinant of Hepatitis B Virus Surface Antigen (HBsAg) and the Corresponding Fragment of the Viral Polymerase in Chronic Virus Carriers Lacking Detectable HBsAg in Serum", Journal of General Virology, vol. 81, 2000, pp. 1165-1174.

* cited by examiner

*Primary Examiner*—Bo Peng
(74) *Attorney, Agent, or Firm*—Sughrue Mion, PLLC

(57) ABSTRACT

An anti-HBs monoclonal antibody is described herein. This antibody can bind to the following: (i) a wild type HBsAg; (ii) at least one mutant HBsAg selected from the group consisting of a first mutant HBsAg and a second mutant HBsAg; and (iii) at least one mutant HBsAg selected from the group consisting of a third mutant HBsAg and a fourth mutant HBsAg. The first mutant HBsAg has a mutation at position 120. The second mutant HBsAg has a mutation at position 141. The third mutant HBsAg has a substitution to a lysine at position 118. The fourth mutant HBsAg has only one mutation at position 144 and an amino acid at the position 144 is substituted by a glutamic acid.

4 Claims, No Drawings

ANTI-HBS MONOCLONAL ANTIBODY

TECHNICAL FIELD

The present invention relates to a monoclonal antibody specifically binding to HBsAg. Specifically, the present invention relates to a monoclonal antibody capable of binding to wild type HBsAg and mutant HBsAg.

BACKGROUND

Hepatitis B virus (HBV) is a double-stranded DNA virus in the family Hepadnaviridae having an envelope that is a lipid bilayer, a nucleocapsid that is a protein, a DNA polymerase, and a genomic DNA. The envelope has S protein, M protein and L protein bound thereto, and a surface antigen (HBsAg) on S protein is involved in viral infection. HBsAg is a polypeptide consisting of 226 amino acids, and in HBsAg, there are 4 kinds of subtypes, that is, adw, ayw, adr and ayr. The adw has lysine as amino acid at each of positions 122 and 160 in HBsAg. The ayw has arginine as amino acid at position 122 and lysine as amino acid at position 160 in HBsAg. The adr has lysine as amino acid at position 122 and arginine as amino acid at position 160. The ayr has arginine as amino acid at each of positions 122 and 160.

Upon HBV infection, HBV releases a large amount of genomic DNA-free spherical or rod-shaped particles (pseudo-particles) into the blood. These particles contain HBsAg. Accordingly, the presence of HBsAg in a blood sample obtained by blood collection can be examined by using an anti-HBs antibody in order to examine the presence of HBV infection.

Since the evolution of viruses such as HBV is rapid, there is a high probability of mutation on the genome. By such mutation on the HBV genome, the amino acid sequence of HBsAg may be mutated to change its structure. When the structure of HBsAg is changed, an anti-HBs antibody used conventionally in HBV diagnosis cannot bind to HBsAg, and thus a patient infected with HBV may be diagnosed to be HBV-negative (false negative). If HBsAg having a mutation (mutant HBsAg) cannot be detected, a HBV host is not only influenced, but infection may also spread thorough afforded blood products and organs. Accordingly, use of anti-HBs antibody capable of binding not only to wild type HBsAg but also to mutant HBsAg is important for examination of HBV.

From this view point, various monoclonal antibodies capable of binding to both wild type HBsAg and mutant HBsAg have been developed so far. For example, a monoclonal antibody described in US2004/0219154A1 can bind to wild type HBsAg and 6 kinds of mutant HBsAgs.

However, various mutant HBsAgs have been reported besides the mutant HBsAgs that can be recognized by the monoclonal antibody described in US2004/0219154A1. There is a demand for development of a monoclonal antibody capable of binding not only to wild type HBsAg but also to mutant HBsAg that could not be detected so far.

SUMMARY

The present invention provides anti-HBs monoclonal antibody.

The scope of the present invention is defined solely by the appended claims, and is not affected to any degree by the statements within this summary.

The anti-HBs monoclonal antibody of the present invention can bind to the following:

(i) a wild type HBsAg;

(ii) at least one mutant HBsAg selected from the group consisting of a first mutant HBsAg and a second mutant HBsAg; and (iii) at least one mutant HBsAg selected from the group consisting of a third mutant HBsAg and a fourth mutant HBsAg.

The first mutant HBsAg has a mutation at position 120 in amino acid sequence in comparison with amino acid sequence of the wild type HBsAg.

The second mutant HBsAg has a mutation at position 141 in amino acid sequence in comparison with amino acid sequence of the wild type HBsAg.

The third mutant HBsAg has a substitution to a lysine at position 118 in amino acid sequence in comparison with amino acid sequence of the wild type HBsAg.

The fourth mutant HBsAg has only one mutation at position 144 in amino acid sequence in comparison with amino acid sequence of the wild type HBsAg and an amino acid at the position 144 is substituted by a glutamic acid.

DESCRIPTION OF THE PREFERRED EMBODIMENTS

The "monoclonal antibody" in this specification includes fragments and derivatives of the monoclonal antibody. Specifically, the fragments and derivatives of the monoclonal antibody are exemplified by Fab, Fab', F(ab)$_2$ and sFv fragment (Blazar et al., 1997, Journal of Immunology, 159:5821-5833 and Bird et al., 1988, Science, 242:423-426). The subclass of the monoclonal antibody is not limited to IgG, and may be IgM or the like.

The "wild type HBsAg" in this specification consists of 226 amino acids and includes every HBsAg recognized generally as wild type. Accordingly, this term encompasses every serotype HBsAg recognized wild type HBsAg.

In this specification, a word "mutation" indicates a mutation of an amino acid in an amino acid sequence in comparison with amino acid sequence of wild type HBsAg.

In this specification, the substitution of original amino acid at position N by amino acid X shall be expressed as "NX". For example, the substitution of original amino acid at position 111 by threonine (T) is expressed as "111T". Further, the substitution of original amino acid X at position N by amino acid Y shall be expressed as "XNY". For example, the substitution of original amino acid threonine (T) at position 118 by lysine (K) is expressed as "T118K".

In this specification, generally used one-letter code of amino acid is sometimes used to indicate the type of amino acid.

The monoclonal antibody in the present embodiment can bind to wild type HBsAg and also to mutant HBsAg that could not be conventionally detected. Specifically, the monoclonal antibody can bind to HBsAg in the following (i) to (iii):

(i) wild type HBsAg, (ii) first mutant HBsAg and/or second mutant HBsAg, and (iii) third mutant HBsAg and/or fourth mutant HBsAg,
   wherein:
   the first mutant HBsAg has a mutation at position 120,
   the second mutant HBsAg has a mutation at position 141,
   the third mutant HBsAg has 118K, and
   the fourth mutant HBsAg is mutant HBsAg having a mutation only at position 144, wherein the mutation is 144E.

Preferably this monoclonal antibody can recognize all of wild type HBsAg, first mutant HBsAg, second mutant HBsAg, third mutant HBsAg and fourth mutant HBsAg.

The mutation at position 120 in the first mutant HBsAg is preferably 120Q or 120T.

The mutation at position 141 in the second mutant HBsAg is preferably 141E.

This monoclonal antibody can bind to preferably at least one member, more preferably all members, selected from the group consisting of:
mutant HBsAg comprising a mutation at position 111,
mutant HBsAg comprising a mutation at position 126,
mutant HBsAg comprising a mutation at position 129,
mutant HBsAg comprising a mutation at position 133,
mutant HBsAg comprising a mutation at position 134,
mutant HBsAg comprising a mutation at position 135,
mutant HBsAg comprising a mutation at position 142,
mutant HBsAg comprising a mutation at position 143,
mutant HBsAg comprising a mutation at position 148,
mutant HBsAg comprising a mutation at position 154, and
mutant HBsAg comprising a mutation at position 155.

This monoclonal antibody can bind to preferably at least one member, more preferably all members, selected from the group consisting of:
mutant HBsAg comprising a mutation at position 111,
mutant HBsAg comprising a mutation at position 126,
mutant HBsAg comprising a mutation at position 129,
mutant HBsAg comprising a mutation at position 133,
mutant HBsAg comprising a mutation at position 134,
mutant HBsAg comprising a mutation at position 135,
mutant HBsAg comprising a mutation at position 142,
mutant HBsAg comprising a mutation at position 143,
mutant HBsAg comprising a mutation at position 145,
mutant HBsAg comprising a mutation at position 148,
mutant HBsAg comprising a mutation at position 154, and
mutant HBsAg comprising a mutation at position 155.

The mutation mentioned above is preferably substitution, deletion or insertion, more preferably substitution.

It is preferable that the mutation possessed by each mutant HBsAg mentioned above is specifically as follows:
The mutation at position 111 is 111T,
the mutation at position 126 is 126S,
the mutation at position 129 is 129H,
the mutation at position 133 is 133L,
the mutation at position 134 is 134A,
the mutation at position 135 is 135S,
the mutation at position 142 is 142S or 142L,
the mutation at position 143 is 143L,
the mutation at position 145 is 145R or 145K,
the mutation at position 148 is 148H,
the mutation at position 154 is 154W, and
the mutation at position 155 is 155Y.

The mutant HBsAg having such mutation was actually specified from serum of a patient infected with HBV and has been reported in literatures etc. Accordingly, the monoclonal antibody capable of binding to these HBsAgs is used in diagnosis of HBV thereby reducing the above-mentioned false negative, as compared with diagnosis using the conventional anti-HBs antibody.

The monoclonal antibody can bind to mutant HBsAg wherein amino acids at and after position 197 were deleted (mutant HBsAg having an amino acid sequence at positions 1 to 196 in wild type HBsAg). That is, an epitope of the monoclonal antibody is present in a region of positions 1 to 196 in HBsAg.

The monoclonal antibody in the present embodiment can be used in immunoassay for detection and/or quantification of HBsAg in a sample suspected of containing wild type and/or mutant HBsAg. Such immunoassay can be used in clinical diagnosis of HBV and in the screening of blood products.

The monoclonal antibody can be obtained by immunizing an animal with HBsAg as antigen by a known immunological method and then using cells of the immunized animal to prepare a hybridoma. "1053 antibody" that is one example of the monoclonal antibodies in the present embodiment is produced by hybridoma "HBs-1053". "149 antibody" that is another example of the monoclonal antibodies in the present embodiment is produced by hybridoma "HBs-149". Hybridomas HBs-1053 and HBs-149 are internationally deposited as Accession Nos. FERM BP-10582 and FERM BP-10583, respectively, under the Budapest Treaty with International Patent Organisms Depository, National Institute of Advanced Industrial Science and Technology, Japan (original deposition date, Apr. 7, 2005; international deposition date, Mar. 27, 2006).

The type of the immunized animal used in preparing the hybridoma is not particularly limited. Specific examples include a mouse, rat, hamster, rabbit, goat and horse, among which a mouse is preferably used. When a mouse is used, its strain is not particularly limited, but BALB/c mouse is preferably used.

The antigen HBsAg can be obtained by purification from a biological sample of a patient infected with HBV. HBsAg can also be obtained by integrating a DNA encoding HBsAg into a plasmid and introducing it into a host cell.

When an animal is immunized with the antigen, an adjuvant is preferably administered. By using the adjuvant, the immune response of the immunized animal to the antigen can be enhanced. The type of the adjuvant is not particularly limited, and for example, Freund complete adjuvant (FCA), Freund incomplete adjuvant (FIA), Ribi (MPL), Ribi (TDM), Ribi (MPL+TDM), *Bordetella pertussis* vaccine, muramyl dipeptide (MDP), aluminum adjuvant (ALUM) etc. are used. Among these, a plurality of adjuvants may be used in combination. Preferably, FCA is used at the time of first immunization, and FIA or Ribi is used at the time of second and the subsequent immunization.

The schedule for immunization can be suitably altered depending on whether the adjuvant is administered or not and according to the type of an animal to be immunized. Hereinafter, the immunization wherein a mouse is used as the immunized animal is described.

In the first immunization, an adjuvant-mixed HBsAg solution is injected intraperitoneally, subcutaneously or intramuscularly. The volume of the adjuvant-mixed HBsAg solution is preferably 0.05 to 1 ml, and the mass of the HBsAg contained therein is preferably 10 to 200 μg. When the adjuvant is not used, an increased amount of HBsAg may be intraperitoneally injected for immunization. Booster immunization is carried out once to 4 times every about 4 to 21 days after the initial administration. About 1 to 4 weeks after the booster immunization, final immunization is carried out. After 3 to 5 days after the final immunization, spleen cells can be separated from the mouse to give antibody-producing cells.

The antibody-producing cells thus prepared are fused with myeloma cells. The origin of myeloma cells is not particularly limited, and those derived from a mouse, rat or human are used, but an animal of the same spices as the immunized animal is preferably used, and an animal of the same species and strain as the immunized animal is more preferably used. When a mouse is used as the origin of myeloma cells, it is preferable to use an established myeloma cell strain such as mouse myeloma P3X63-Ag8, P3X63-Ag8-U1, P3NS1-Ag4, SP2/o-Ag14 or P3X63-Ag8•653. Some myeloma cells produce an immunoglobulin light chain, and when such myeloma cell is used as a subject of fusion, this light chain may be bound to an immunoglobulin heavy chain produced by the antibody-producing cell. Accordingly, a myeloma cell not producing an immunoglobulin light chain, for example, P3X63-Ag8•653 or SP/o-Ag14 is preferably used.

The method of producing a hybridoma by fusing the antibody-producing cell with the myeloma cell is not particularly limited, and a known method can be used. Examples include a method of using polyethylene glycol (PEG method), a method of using Sendai virus and a method of using an electric fusion apparatus. In the PEG method, spleen cells and myeloma cells may be suspended in a mixing ratio of from 1:1 to 10:1, preferably from 5:1 to 10:1 in a suitable medium or buffer containing about 30 to 60% PEG (average molecular weight 1000 to 6000) and then incubated for about 30 seconds to 3 minutes under the conditions of a temperature of about 25 to 37° C. and pH 6 to 8. After the incubation is finished, the cells can be washed to remove the PEG solution, suspended again in a hypoxanthine-thymidine medium (HT medium) or the like, then seeded in, for example, a microtiter plate and continued to be cultured.

The cells after fusion are cultured in a selective medium and selected for hybridoma. The selective medium is not particularly limited insofar as in the medium, the parent cell strain perishes and only the fusion cells can grow. Usually, a hypoxanthine-aminopterin-thymidine medium (HAT medium) is used. Selection of the hybridoma is initiated by exchanging apart of the medium, preferably about half of the medium, with the selective medium, usually 1 to 7 days after the fusion procedure, and culturing the cells while the medium is exchanged repeatedly every 2 to 3 days in the same manner.

Whether the growing hybridoma produces a desired antibody or not can be confirmed by collecting a culture supernatant and performing an antibody titer assay. The antibody titer assay is not particularly limited and a known method can be used. For example, the above supernatant diluted serially is added to, and reacted with, an immobilized antigen and further reacted with a secondary antibody (anti-globulin antibody, anti-IgG antibody, anti-IgM antibody etc.) labeled with a fluorescence substance, an enzyme, or a radioisotope (RI), whereby the antibody produced in the supernatant can be detected and the antibody titer can be measured. By screening the culture supernatant in each well of a plate, a hybridoma producing the desired antibody can be obtained.

Then, a single clone is separated. The separation method is not particularly limited, and a known method can be used. Examples include a limiting dilution method, a soft agar method, a method of using a fluorescence-activated cell sorter, etc. In the limiting dilution method, for example, a hybridoma colony is diluted serially with a medium so as to be about 1 cell/well and then cultured, whereby a hybridoma clone producing the objective monoclonal antibody can be isolated. When the resulting hybridoma clone is frozen in the presence of a cryoprotectant such as approx. 10 w/v % dimethyl sulfoxide (DMSO), glycerin or the like and stored at −196° C. to −70° C., the hybridoma clone can be stored semi-permanently. The cells can be used after rapidly thawed in a thermostatic bath at about 37° C. at use. The cells are used preferably after they are sufficiently washed such that the cytotoxicity of the cryoprotectant does not remain.

For examining the immunoglobulin subclass of the antibody produced by the hybridoma, the hybridoma is cultured under general conditions, and the antibody secreted into its culture supernatant may be examined by using a commercially available kit for determination of antibody class/subclass.

The method used in obtaining a monoclonal antibody from the hybridoma is suitably selected depending on a necessary amount and the properties of the hybridoma. Examples include a method of obtaining a monoclonal antibody from ascitic fluid of a mouse transplanted with the hybridoma, a method of obtaining a monoclonal antibody from a culture supernatant obtained by cell culture, etc. Insofar as the hybridoma can grow in the abdomen of the mouse, the monoclonal antibody can be obtained at a high concentration of several mg/ml from the ascitic fluid. The hybridoma not capable of growing in vivo is obtained from a culture supernatant in cell culture. The method of obtaining the monoclonal antibody in cell culture is advantageous over a method conducted in vivo in that although the amount of the antibody produced is low, formation of the antibody is easy with less contamination with immunoglobulins and other contaminants contained in the mouse abdomen.

When the monoclonal antibody is obtained from ascitic fluid of a mouse transplanted with the hybridoma, the hybridoma is transplanted in the abdomen of a BALB/c mouse to which a substance possesses immunosuppressant properties, such as pristane (2,6,10,14-tetramethylpentadecane), has previously been administered, and after about 1 to 3 weeks, the ascitic fluid accumulated therein is collected. In the case of a hybridoma obtained by fusing cells from animals of different animal species (for example, mouse and rat), it is preferable to use a nude mouse, a radiation-treated mouse, etc.

When the antibody is obtained from the cell culture supernatant, it is possible to use, for example, culture methods used in maintaining cells, such as a stationary culture method, a high-density culture method and a spinner flask culture method. By using any of these methods, the hybridoma is cultured to give a culture supernatant containing the antibody.

Purification of the monoclonal antibody from the ascitic fluid or culture supernatant can be carried out by using a known immunoglobulin purification method. The immunoglobulin purification method is not particularly limited, and examples include a fractionation of using ammonium sulfate or sodium sulfate, a PEG fractionation, an ethanol fractionation, a DEAE ion-exchange chromatographic method and a gel filtration method.

When the monoclonal antibody is mouse IgG, the antibody can be purified by affinity chromatography with a protein A-bound carrier or an anti-mouse immunoglobulin-bound carrier.

The monoclonal antibody can be used in immunoassay for detection and/or quantification of HBsAg contained in a biological sample as a sample to be examined. Such assay can be used in diagnosis of HBV and in screening of blood products. The immunoassay is carried out by mixing the monoclonal antibody in the present embodiment with a sample and then confirming the presence of a monoclonal antibody/HBsAg complex therein.

EXAMPLES

Experiment 1

(1) Preparation of Monoclonal Antibody 1-1. Immunization of Mouse

100 μl FCA was added to, and mixed with, 100 μl PBS containing 50 μg inactivated adr-type HBsAg (manufactured by TRINA) purified from human serum, and then emulsified by Vortex to prepare 200 μl FCA-mixed HBsAg solution. Separately, 200 μl FIA-mixed HBsAg solution was prepared in the same manner except that FIA was used in place of FCA.

First immunization was carried out by intraperitoneally administering 200 µl of the FCA-mixed HBsAg solution to an 8-week-old male BALB/c mouse. After the first immunization, booster immunization with 200 µl of the FIA-mixed HBsAg solution was carried out 5 times every 2 weeks. Four days after the final booster immunization, the spleen cells were separated and then fused with P3X63-Ag8•653 mouse myeloma cells by the PEG method to prepare a hybridoma.

1-2. Culture of the Hybridoma

The hybridoma was suspended at $2.5 \times 10^6$ cells/ml in HT medium and pipetted to each well of a 96-well plate (hereinafter, referred to as culture plate, manufactured by Corning) at $2.5 \times 10^5$ cells/well. The culture plate was left in a thermostatic chamber at 37° C. in 5% $CO_2$ to initiate culture the hybridoma. On the next day, 25 µg HAT medium was added to each well of the culture plate, and culture was further continued. When hybridoma colonies appeared by culture for 10 days, screening of a hybridoma producing the monoclonal antibody was carried out.

1-3. Screening of the Hybridoma adr-Type HBsAg (manufactured by TRINA) was added at a concentration of 0.5 µg/ml to 0.1 M PBS (pH 7.5) containing 0.1 w/v % $NaN_3$, to prepare an HBsAg solution for immobilization. 100 µl of the HBsAg solution for immobilization was pipetted into each well of a 96-well plate (manufactured by NUNC, hereinafter, referred to as antigen-immobilized plate). The plate was left overnight at 4° C. and then washed 3 times with TBS buffer solution containing Tween 20 at a concentration of 0.05% (hereinafter, referred to as first buffer solution). After washing, 300 µl TBS buffer solution containing BSA at a concentration of 2 w/v % (hereinafter, referred to as second buffer solution) was added to each well of the antigen-immobilized plate and left for 2 hours at room temperature.

75 µl of the second buffer solution was added to each well of the antigen-immobilized plate. The hybridoma culture supernatant prepared in 1-2 above was removed from each well of the culture plate and then added at a volume of 25 µl/well to each well of the antigen-immobilized plate. After the second buffer solution and the culture supernatant were added, the antigen-immobilized plate was incubated at 37° C. for 1 hour. After incubation, each well of the antigen-immobilized plate was washed with 300 µl of the first buffer solution. After washing, 100 µl horseradish peroxidase-labeled anti-mouse Ig polyclonal antibody (Code No. P0447, manufactured by DAKO) diluted 10000-fold with the second buffer solution was added to each well of the antigen-immobilized plate. The mixture was incubated at room temperature for 30 minutes, then each well of the antigen-immobilized plate was washed with 300 µl of the first buffer solution, and positive wells were detected by using TMB peroxidase EIA Substrate kit (manufactured by Bio-Rad). As a result, it was confirmed that anti-HBs monoclonal antibodies were produced in about 300 of 2688 wells.

(2) Preparation of Mutant HBsAg

HBV DNA was prepared from blood samples of patients infected with HBV having wild type HBsAg (subtype: adr type), and a DNA fragment containing a region encoding wild type HBsAg was amplified by PCR. The amino acid sequence of wild type HBsAg encoded by this DNA fragment is shown in SEQ ID NO: 1. This DNA fragment was integrated into a eucaryotic cell expression vector pcDNA3.1(+) (Invitrogen) to prepare a wild type HBsAg expression plasmid. Then, site-specific mutation with this expression plasmid as a template was carried out using Quick Change Site-Directed Mutagenesis Kit (Stratagene), to construct plasmids capable of expressing 20 kinds of mutant HBsAg (mutant HBsAg #1 to #20) shown in Table 1 below. The wild type HBsAg expression plasmid and mutant HBsAg expression plasmids were purified by EndoFree Plasmid Maxi Kit (QIAGEN). After purification, each expression plasmid was introduced into a monkey kidney-derived COS7 cell by using PolyMagII (OZ Bioscience), and the cell was cultured for 24 hours in a 5% $CO_2$ incubator. As the negative control, COS7 cells into which pcDNA3.1(+) alone had been introduced without integrating HBsAg-coding DNA were prepared and similarly cultured.

TABLE 1

| | Mutation |
|---|---|
| wild type HBsAg | — |
| mutant HBsAg #1 | P111T |
| mutant HBsAg #2 | T118K |
| mutant HBsAg #3 | P120Q |
| mutant HBsAg #4 | P120T |
| mutant HBsAg #5 | I126S |
| mutant HBsAg #6 | Q129H |
| mutant HBsAg #7 | M133L |
| mutant HBsAg #8 | F134A |
| mutant HBsAg #9 | P135S |
| mutant HBsAg #10 | K141E |
| mutant HBsAg #11 | P142L |
| mutant HBsAg #12 | P142S |
| mutant HBsAg #13 | S143L |
| mutant HBsAg #14 | D144A |
| mutant HBsAg #15 | D144E |
| mutant HBsAg #16 | G145R |
| mutant HBsAg #17 | G145K |
| mutant HBsAg #18 | T148H |
| mutant HBsAg #19 | S154W |
| mutant HBsAg #20 | S155Y |

(3) Selection of Antibodies Reacting with HBsAg

The COS7 cells prepared in (2) were peeled from a Petri dish with a Trypsin-EDTA solution (manufactured by Sigma) and washed with PBS. After washing, the cells were suspended in a suitable amount of PBS to prepare a fluid having cells suspended therein. The fluid having cells suspended therein was spotted in a suitable amount on a slide glass, then air-dried and fixed with acetone (manufactured by Wako Pure Chemical Industries, Ltd.). Each of culture supernatants of the about 300 anti-HBs monoclonal antibody-containing clones prepared in (1) was reacted with the slide glass after fixation with acetone. The reactivity of each monoclonal antibody to the wild type HBsAg and the 20 types of mutant HBsAgs was determined with FITC-labeled anti-mouse Ig antibody by observation under a fluorescence microscope. As a result, broad reactivity was recognized in 1053 antibody produced by hybridoma HBs-1053 (Deposition No. FERM BP-10582) and 149 antibody produced by hybridoma HBs-149 (Deposition No. FERM BP-10583).

TABLE 2

| | 149 antibody | 1053 antibody |
|---|---|---|
| Negative Control | − | − |
| wild type HBsAg | + | + |
| mutant HBsAg #1 (P111T) | + | + |
| mutant HBsAg #2 (T118K) | + | + |
| mutant HBsAg #3 (P120Q) | + | + |
| mutant HBsAg #4 (P120T) | + | + |

TABLE 2-continued

|  | 149 antibody | 1053 antibody |
|---|---|---|
| mutant HBsAg #5 (I126S) | + | + |
| mutant HBsAg #6 (Q129H) | + | + |
| mutant HBsAg #7 (M133L) | + | + |
| mutant HBsAg #8 (F134A) | + | + |
| mutant HBsAg #9 (P135S) | + | + |
| mutant HBsAg #10 (K141E) | + | + |
| mutant HBsAg #11 (P142L) | + | + |
| mutant HBsAg #12 (P142S) | + | + |
| mutant HBsAg #13 (S143L) | + | + |
| mutant HBsAg #14 (D144A) | + | + |
| mutant HBsAg #15 (D144E) | + | + |
| mutant HBsAg #16 (G145R) | − | + |
| mutant HBsAg #17 (G145K) | − | + |
| mutant HBsAg #18 (T148H) | + | + |
| mutant HBsAg #19 (S154W) | + | + |
| mutant HBsAg #20 (S155Y) | + | + |

In Table 2, "+" indicates that the antibody has recognized, and bound to, the antigen, while "−" indicates that the antibody/antigen reaction did not occur.

As can be seen from Table 2, the 149 antibody has bound to the wild type HBsAg and all the mutant HBsAgs excluding the mutant HBsAg having a mutation on amino acid at position 145. The 1053 antibody has bound to all the mutant HBsAgs and the wild type HBsAg shown in Table 1.

Experiment 2

A DNA encoding an amino acid sequence of from position 1 to position 196 in wild type HBsAg (subtype: adr) was prepared by PCR with wild type HBsAg DNA as a template and then integrated in a eucaryotic cell expression vector pcDNA3.1 (+) to prepare a wild type HBsAg expression plasmid. This plasmid was introduced into a COS7 cell which was then cultured for 24 hours in a 5% $CO_2$ incubator. This COS7 cell can express HBsAg from which amino acids at and after position 197 were deleted (hereinafter, referred to as C terminal-deleted HBsAg).

Whether the 148 antibody and 1053 antibody reacted with the C terminal-deleted HBsAg was evaluated in the same manner as in EXPERIMENT 1. The determination results are shown in Table 3 below.

TABLE 3

(1) C terminal-deleted HBsAg

|  | 149 antibody | 1053 antibody |
|---|---|---|
| Negative Control | − | − |
| C terminal-deleted HBsAg | + | + |

From Table 3, it was confirmed that the 149 antibody and 1053 antibody can recognize the C terminal-deleted HBsAg. From this result, it was revealed that an epitope of each of the 149 antibody and 1053 antibody is present in a region of positions 1 to 196 in HBsAg.

What is claimed is:

1. A hybridoma deposited with International Patent Organism Depositary of Advanced Industrial Science and Technology under Deposit No FERM BP-10582.

2. A monoclonal antibody produced by the hybridoma of claim 1.

3. A hybridoma deposited with International Patent Organism Depositary of Advanced Industrial Science and Technology under Deposit No. FERM BP-10583.

4. A monoclonal antibody produced by the hybridoma of claim 3.

* * * * *

SEQUENCE LISTING

```
<160> NUMBER OF SEQ ID NOS: 1

<210> SEQ ID NO 1
<211> LENGTH: 226
<212> TYPE: PRT
<213> ORGANISM: Hepatitis B virus

<400> SEQUENCE: 1

Met Glu Asn Thr Thr Ser Gly Phe Leu Gly Pro Leu Leu Val Leu Gln
1               5                   10                  15

Ala Gly Phe Phe Leu Leu Thr Lys Ile Leu Thr Ile Pro Gln Ser Leu
                20                  25                  30

Asp Ser Trp Trp Thr Ser Leu Asn Phe Leu Gly Gly Ala Pro Thr Cys
            35                  40                  45

Pro Gly Gln Asn Ser Gln Ser Pro Thr Ser Asn His Ser Pro Thr Ser
    50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Leu Pro Gly
            100                 105                 110

Thr Thr Thr Thr Ser Thr Gly Pro Cys Lys Thr Cys Thr Ile Pro Ala
        115                 120                 125

Gln Gly Thr Ser Met Phe Pro Ser Cys Cys Thr Lys Pro Ser Asp
    130                 135                 140

Gly Asn Cys Thr Cys Ile Pro Ile Pro Ser Ser Trp Ala Phe Ala Arg
145                 150                 155                 160
```

```
-continued

Phe Leu Trp Glu Trp Ala Ser Val Arg Phe Ser Trp Leu Ser Leu Leu
            165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Asn Ile
            195                 200                 205

Leu Ser Pro Phe Leu Pro Leu Leu Pro Ile Phe Phe Cys Leu Trp Val
        210                 215                 220

Tyr Ile
225
```